United States Patent
Loeb et al.

(10) Patent No.: US 7,593,776 B2
(45) Date of Patent: Sep. 22, 2009

(54) FLEXIBLE COMMUNICATION AND CONTROL PROTOCOL FOR A WIRELESS SENSOR AND MICROSTIMULATOR NETWORK

(75) Inventors: Gerald E. Loeb, South Pasadena, CA (US); Jack Weissberg, Culver City, CA (US); Nuria Rodriguez, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/773,322

(22) Filed: Jul. 3, 2007

(65) Prior Publication Data
US 2008/0140154 A1    Jun. 12, 2008

Related U.S. Application Data

(60) Provisional application No. 60/806,588, filed on Jul. 5, 2006.

(51) Int. Cl.
*H04L 5/16* (2006.01)
*A61N 1/08* (2006.01)
*A61N 1/372* (2006.01)

(52) U.S. Cl. .............. 607/60; 607/30; 607/48; 600/300; 375/222

(58) Field of Classification Search ............ 607/30, 607/36, 48, 60; 600/300; 375/222, 519
See application file for complete search history.

(56) References Cited

U.S. PATENT DOCUMENTS

| | | | |
|---|---|---|---|
| 4,390,022 A * | 6/1983 | Calfee et al. ............ 607/16 |
| 5,193,539 A | 3/1993 | Schulman | |
| 5,193,540 A | 3/1993 | Schulman | |
| 5,312,439 A | 5/1994 | Loeb | |
| 5,324,316 A | 6/1994 | Schulman | |
| 5,405,367 A | 4/1995 | Schulman | |
| 5,864,580 A * | 1/1999 | Lowe et al. ............ 375/222 |
| 6,044,297 A * | 3/2000 | Sheldon et al. ............ 607/17 |
| 6,083,248 A * | 7/2000 | Thompson ............ 607/30 |

(Continued)

OTHER PUBLICATIONS

Cameron, T. et al. Micromodular implants to provide electrical stimulation of paralyzed muscles and limbs, IEEE Trans Biomed Eng 1997; 44: pp. 781-790.

(Continued)

*Primary Examiner*—Carl H Layno
*Assistant Examiner*—Natasha N Patel
(74) *Attorney, Agent, or Firm*—McDermott Will & Emery LLP

(57) ABSTRACT

A novel system and method for restoring functional movement of a paralyzed limb(s) or a prosthetic device. Stimulating one or more muscles of a patient using an implanted neuromuscular implants and sensing the response of the stimulated muscle by the implants, wherein the sensing response is not limited to data related to patient's movement intention, the posture, muscle extension, M-Wave and EMG. A communication and control protocol to operate the system safely and efficiently, use of forward and reverse telemetry channels having a limited bandwidth capacity, and minimizing the adverse consequences caused by errors in data transmission and intermittent loss of power to the implants. Adjusting stimulation rates and phases of the stimulator in order to achieve an efficient control of muscle force while minimizing fatigue and therefore providing for smooth movements and dynamic increase of the strength in patient's muscle contraction.

78 Claims, 6 Drawing Sheets

U.S. PATENT DOCUMENTS

2004/0059392 A1* 3/2004 Parramon et al. ............ 607/36
2005/0197680 A1* 9/2005 DelMain et al. ............... 607/60

OTHER PUBLICATIONS

Falcon, C. Inside implantable Devices. Medical Design Technology, Oct. 2004. pp. 24-27.

Gudnason, G. et al. A chip for an implantable neural stimulator. Analog Integrated Circuits and Signal processing 22 (1999), pp. 81-89.

Gudnason, G. et al. A distributed transducer system for functional electrical stimulation. Proc. ICECS, Malta, vol. 1, (2001) pp. 397-400.

Kaliki, .RR. et al. The Effects of Training Set on Prediction of Elbow Trajectory from Shoulder Trajectory during Reaching to Targets. 28th Annual International conference IEEE Engineering in Medicine and Biological Society (EBMS), pp. 5483-5486.

Lee, S.Y. An implantable wireless bidirectional communication microstimulator for neuromuscular stimulation. IEEE Transactions on circuits and systems, vol. 52, Dec. 2005, pp. 2526-2538.

Liu, W. et al. A Neuro-Stimulus Chip with Telemetry Unit for Retinal Prosthetic Device. IEEE Journal of Solid-State Circuits, vol. 35 Oct. 2000, pp. 1487-1497.

Loeb, G. E. et al. The Motor Unit and Muscle Action. Principles of Neural Science, 4th Ed Mc Graw Hill 2000, Chapter 34, pp. 674-694.

Loeb. G. E. et al. BION Injectable Interfaces with Peripheral Nerves and Muscles. Neurosurgical Focus, vol. 20, May 2006, pp. 1-9.

Sachs, N.A. et al. Development of a BIONic Muscle Spindle for Prosthetic Proprioception. IEEE Trans. Biomedical Engineering, vol. 54, No. 6, Jun. 2007, pp. 1031-1041.

Salter, A.C.D. et al. First clinical experience with BION implants for therapeutic electrical stimulation. Neuromodulation 7, 2004, pp. 38-47.

Sivard, A. et al. Challenges of in-body communications. Embedded Systems Europe, Mar. 2005, pp. 34-37.

Suaning, G.J. et al. CMOS Neurostimulation ASIC with 100 Channels, Scaleable Output and Bidirectional Radio-Frequency; Telemetry. IEEE Transactions on Biomedical Engineering, vol. 48, Feb. 2001, pp. 248-260.

Tan, W. et al. Feasibility of Prosthetic Posture Sensing Via Injectable Electronic Modules. IEEE Trans. Neural Systems & Rehab. Engineering, vol. 15, No. 2, Jun. 2007, pp. 295-309.

Zhang C et al ("A wideband frequency-shift keying demodulator for wireless neural stimulation microsystems", Journal of Zheijiang University Science A, 2006 7 (6): 1056-1060).

Zou, Q. et al. Single- and Triaxis Piezoelectric-Bimorph Accelerometer. IEEE/ASME Journal of Microelectromechanical Systems, vol. 17, No. 1, Feb. 2008, pp. 45-57.

* cited by examiner

_US 7,593,776 B2_

FLEXIBLE COMMUNICATION AND CONTROL PROTOCOL FOR A WIRELESS SENSOR AND MICROSTIMULATOR NETWORK

CROSS-REFERENCE TO RELATED APPLICATIONS

This application claims the benefit of filing date of U.S. Provisional Application No. 60/806,588 filed on Jul. 5, 2006, entitled "Flexible Communication and Control Protocol for a Wireless Sensor and Microstimulator Network", the contents of which are incorporated by reference.

STATEMENT OF GOVERNMENT RIGHTS

This invention was made with government support under Contract No. R01 EB002094 awarded by the National Institutes of Health and Contract No. EEC-0310723 awarded by the National Science Foundation. The government has certain rights in the invention.

BACKGROUND

1. Field

This application relates generally to devices and methods for electrical stimulation of biological tissues, and in particular a protocol for flexible communication and control of implanted wireless sensor(s) and microstimulator(s) within the body.

2. Description of Related Art

Electrical signals can be generated within specific tissues by means of miniature implanted capsules, referred to as a "microstimulator", that receive power and control signals by inductive coupling of magnetic fields generated by an extracorporeal antenna rather than requiring any electrical leads. See, for example, U.S. Pat. Nos. 5,193,539; 5,193,540; 5,324,316; and 5,405,367, each of which is incorporated in its entirety by reference herein. These microstimulators are particularly advantageous because they can be manufactured inexpensively and can be implanted non-surgically by injection. Additionally, each implanted microstimulator can be commanded, at will, to produce a well-localized electrical current pulse of a prescribed magnitude, duration and/or repetition rate sufficient to cause a smoothly graded contraction of the muscle in which the microstimulator is implanted. Further, operation of more than one microstimulator can be coordinated to provide simultaneous or successive stimulation of large numbers of muscles, even over long periods of time.

A microstimulator system is typically composed of a control unit external to the body and several individual microstimulators implanted in the patient which electrically stimulate each muscle. Each microstimulator receives power and data from a transmitter coil worn over the limb and shaped to power all the devices simultaneously. This coil is connected to an external controller that has been programmed to control the movement of the limb. The microstimulators may also performing sensing functions, and such information may be transmitted back to the controller so that the controller can adjust the stimulation parameters.

However, current microstimulator systems present difficulties in controlling stimulation. In particular, it can be difficult to control stimulation of muscles to provide smooth movements and to dynamically increase the strength of muscle contraction. In addition, communication errors between the controller and the microstimulators may cause harm to the patient, such as excessive muscle contraction.

SUMMARY

Exemplary embodiments of the biomedical network control systems described herein can be used to control a paralyzed hand or prosthetic systems having a network of sensors, actuators, and a controller. The control mechanisms can avoid the above shortcomings, among others, by providing flexible configuration and dynamic adjustment of sensors and actuators. Techniques are described to optimize performance and reliability within the constraints of bandwidth required for efficient operation of medical devices.

Exemplary embodiments may be used to control power and stimulation in systems comprising implantable microstimulators. Exemplary systems include a synchronous, full duplex, connection oriented protocol, which can be used in a centralized control system that requires a relatively high data rate (for example, up to 480 Kbps). The protocol can be implemented to be compatible with MICS requirements (Medical Implant Communication Service) and its limitations on overall channel bandwidth.

In exemplary biomedical stimulation systems, sensors may be controlled by combining global signaling and registers included in implanted microstimulators. The "frame sync" and "internal sync" signals may be implemented through Manchester code violations. The combination of signals and registers (the combination being referred to as "sync mask") can allow control of the stimulation and the sensors included in the implants in order to dynamically adjust the precision of sensors, to smooth movements and to increase dynamically the strength in muscle contraction.

Exemplary embodiments may also provide protection against errors in communications that may otherwise harm the patient. In such embodiments, a "dynamic mask" may be implemented to avoid excessive muscle contraction, which may be caused by errors in the bits of data used to configure stimulation parameters.

It is understood that other embodiments of the devices and methods will become readily apparent to those skilled in the art from the following detailed description, wherein it is shown and described only exemplary embodiments of the devices, methods and systems by way of illustration. As will be realized, the devices, systems and methods are capable of other and different embodiments and its several details are capable of modification in various other respects, all without departing from the spirit and scope of the invention. Accordingly, the drawings and detailed description are to be regarded as illustrative in nature and not as restrictive.

BRIEF DESCRIPTION OF THE DRAWINGS

Aspects of the biomedical network control systems are illustrated by way of example, and not by way of limitation, in the accompanying drawings, wherein.

DETAILED DESCRIPTION

The detailed description set forth below in connection with the appended drawings is intended as a description of exemplary embodiments and is not intended to represent the only embodiments in which the biomedical stimulation devices, methods and systems can be practiced. The term "exemplary" used throughout this description means "serving as an example, instance, or illustration," and should not necessarily be construed as preferred or advantageous over other embodiments. The detailed description includes specific details for the purpose of providing a thorough understanding the biomedical network control systems. However, it will be apparent to those skilled in the art that the biomedical stimulation devices, methods and systems may be practiced without these specific details.

Figure 1:
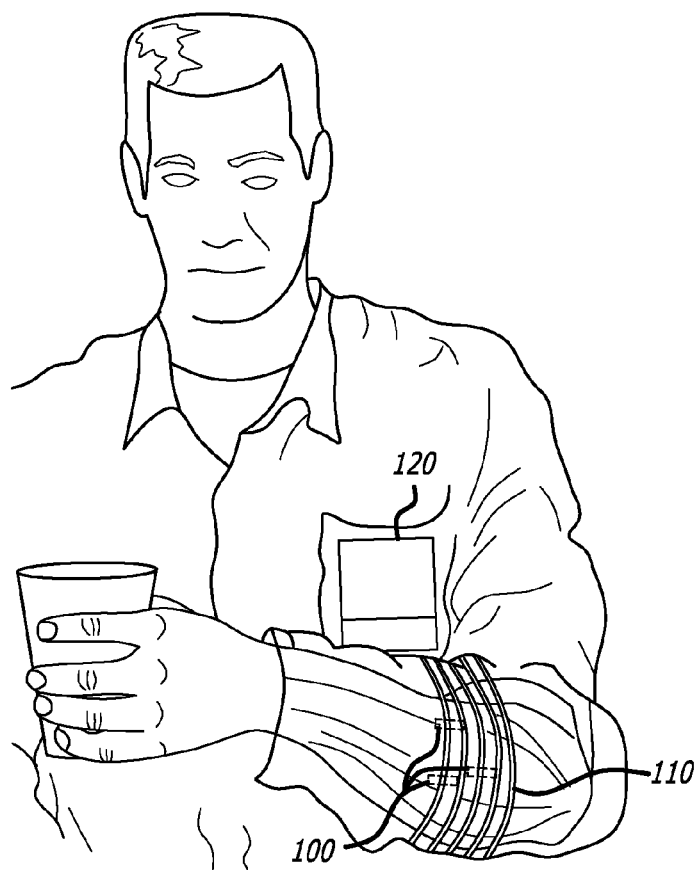
FIG. 1 illustrates an exemplary biomedical microstimulator system overview.

Electrical stimulation is a rehabilitation therapy that has been widely used to exercise weak and paralyzed muscles, nerves or any other tissues in order to prevent or reverse disuse atrophy. The microstimulator system as depicted in FIG. 1 includes individually addressable, wireless microstimulators 100 that can be injected into one or more muscles or nerves or other tissues of a paralyzed hand to control their activation, thus avoiding the discomfort of trancutaneous stimulation and the invasiveness of surgically implanted multichannel stimulators (see for example, Cameron T, Loeb G E, Peck R A, Scgyknab J H, Strojnic P, Troyk P R, *Micromodular implants to provide electrical stimulation of paralyzed muscles and limbs*, IEEE Trans Biomed Eng 1997; 44: 781-790; the contents of which are incorporated herein by reference). The system further includes an externally worn coil and coil driver 110 that transmits power and command signals inductively to a coil in each of the microstimulators 100. The system command and control is performed by the external control unit 120. In some exemplary embodiments the control unit may be an internal unit installed within the patient's body.

One Example of an implantable biomedical stimulator which may benefit from charge-regulated stimulus control is the BION™ (BIONic Neurons; Alfred E. Mann Institute, University of Southern California). BIONs™ are a class of implantable medical device: separately addressable, single channel, electronic microstimulators (16 mm long×2 mm in diameter), that can be injected in or near muscles and nerves to treat paralysis, spasticity and other neurological dysfunctions. Microstimulators that may be used in various embodiments are described in U.S. Pat. Nos. 5,193,539; 5,193,540; 5,312,439; and 5,324,316, each of which are incorporated by reference in their entirety.

The BION1 system has been used successfully for rehabilitation of patients with various consequences of disuse atrophy (see Dupont Salter A C, Bagg S D et al., "*First clinical experience with BION implants for therapeutic electrical stimulation*", Neuromodulation 7, 2004, pp 38-47 and Loeb G E, Richmond F J R et al., "*BION Injectable Interfaces with Peripheral Nerves and Muscles*", Neurosurgical Focus, Vol 20:1-9, May 2006).

Use of neuromuscular electrical stimulation to recover the functional movement of a limb (functional electrical stimulation; FES) requires the generation of sequences of muscle contractions that are not predictable and are likely to need real-time control.

The new BION2 implants include several types of electrical, magnetic and mechanical sensors for limb posture and trajectory (Described in Zou Q, Tan W et al, "Single-axis and Tri-axis Piezoelectric Bimorph Accelerometer", IEEE/ASME Journal of Microelectromechanical Systems, in press, Tan W and Loeb G E, "Feasibility of prosthetic posture sensing via injectable electronic modules", IEEE Trans. Neural Systems & Rehab. Engng., in press, and Sachs N A and Loeb, G E, "Development of a BIONic muscle spindle for prosthetic proprioception", IEEE Trans. Biomedical Engineering, in press).

Information obtained from a residual voluntary limb movement can be used to derive commands signaling the intentions of the operator/patient (see Kaliki R R, Davoodi R et al, "The Effects of Training Set on Prediction of Elbow Trajectory from Shoulder Trajectory during Reaching to Targets", 28th Annual International conference IEEE Engineering in Medicine and Biological Society (EMBS), pp 5483-5486). Information about the posture and trajectory of the limb produced by the FES can be used to adjust the muscle stimulation parameters, much as the central nervous system that normally uses reflexes in order to adjust motor neuron activity. Some systems provide stimulation and sensing in different devices (see Gudnason G, Nielsen et al, "A distributed transducer system for functional electrical stimulation", Proc. ICECS, Malta, vol. 1, pp. 397-400, 2001). However by collocating stimulation and sensing functions in the same BION2 implants, the number of different devices that are needed can be minimized. This may lead to fewer number of implants required in a given patient. This mandates a system design in which general purpose implants can be configured flexibly to meet the requirements of a wide range of clinical applications and then controlled dynamically during the performance of motor tasks.

As discussed below we present the architecture and communication protocol of the BION2 system in the context of the physiological properties of the neuromusculoskeletal system that is to be controlled, the clinical requirements and the hardware capabilities of the BION2 implants.

We also present the essential features of the protocol and some innovative features of our system. In addition, we will present the output of a complete digital simulation of an application-specific custom IC (ASIC) in the implants and a field-programmable gate array (FPGA) in the external controller.

I) Physiological Considerations

The function of a BION system is constrained by the properties of the neuromusculoskeletal system with which it must interact. As the brain learns to control the limbs in infancy, it is effectively performing system identification and developing strategies for dealing with the system that it discovers. In order to build upon those natural strategies, biomimetic design principles have been chosen to be applied where possible, considering how the prosthetic hardware can replace missing functions and enable the reuse of control strategies that have been studied in intact subjects.

A) Control of Muscle Activation

Muscles are composed of hundreds of thousands of individual fibers that are organized into a few hundred motor units, each controlled by a separate motor neuron. Muscle force depends on the number of motor units that have been recruited and their frequencies of firing, as well as nonlinear effects of the length and velocity of motion (shortening or stretching) of the muscle fibers (see Loeb G E and Ghez C, "The Motor Unit and Muscle Action", Principles of Neural Science, 4th Ed Mc Graw Hill 2000, Chapter 34, pp 674-694).

BIONs are usually implanted near the entry zone of the nerve containing the motor axons, where increasing the intensity of pulsatile stimuli can recruit an increasing percentage of the motor units. Stimulus efficacy is generally proportional to the charge delivered with each pulse, the product of pulse current and pulse duration. All recruited motor units fire synchronously at the stimulus pulse repetition rate, rather than the asynchronous, smooth modulation typical of physiological recruitment (typically 10-40 Hz). If the stimulus rate is set too high, the recruited muscle fibers will fatigue quickly. If it is set too low, the force produced by the muscle may have a substantial ripple at the stimulus rate and it will be difficult to ramp up force quickly or to achieve brief maximal effort such as for responding to perturbations.

Limb motion is the result of coordinated activity in many muscles with different combinations of actions at joints with varying degrees of freedom. Most muscles cross more than one joint, act on more than one axis of motion, and have moment arms that depend complexly on joint angles. Because muscles can pull but not push, control of joint motion depends on the relative recruitment of antagonistically arranged muscle groups. Because active muscles have spring-like (length-dependent) and dashpot-like (velocity-dependent) contractile properties, contraction of antagonistic muscles can be used to alter the impedance of joints independently from their net torque on the joint.

B) Feedback Signals

Biological muscles are endowed with a variety of sense organs, most prominently including Golgi tendon organs, which sense muscle force, and muscle spindles, which sense combinations of length and velocity that can be adjusted dynamically by the fusimotor gain control system. These signals are combined with those from cutaneous sensors and with the descending command signals from the brain in a sophisticated set of excitatory and inhibitory interneurons in the spinal cord that provide much of the input to the motor neurons. This somatosensory information also projects up to the brain, where it is combined with other sensory modalities such as the acceleration and orientation of the head with respect to gravity.

The response time of the biological system to perturbations is limited by physiological constraints. Both sensory and motor nerve fibers conduct at approximately 50 ms in humans, so the transit delay to and from the spinal cord is on the order of 20-30 ms. Muscle fibers respond sluggishly to changes in their neural activation with time constants of about 50 ms (rising phase) and 100 ms (falling phase) to step changes in that activation. There are also various central delays (1-100 ms) while the interneuronal system computes the desired responses at various levels of the spinal cord and brain with varying degrees of integration with other signals (e.g. considerations of interlimb coordination, postural balance, visual feedback, etc.). These delays pose serious challenges for the use of closed-loop control in both biological and prosthetic systems but they provide useful hints about specifications of a biomimetic communication and control scheme (see below). They must be considered in the context of the natural mechanical resonances of the limb, which are restricted by the substantial inertial mass of the limb segments.

II) Clinical Requirements

The capability requirement of each BION2 implant can be summarized as:
1. to sense patient intention;
2. to activate the muscle by causing contraction and measuring the contraction effectiveness;
3. to sense posture and movement in various coordinate frames; and
4. to communicate all sensed data to the controller and receive new stimulation commands.

As discussed below, the clinical requirements for BION2 system are related to the wide variety of applications, the number of muscles involved in the applications and the safety of operation required.

A) Range of Applications

In some embodiments, BIONs are not typically intended for a single anatomical site or clinical application. Rather, they can be general-purpose modules intended to be injected where and when they are needed and combined in virtually unlimited ways to support functions that may not have been considered when the system was designed. In fact, BION2 implants may be used to detect myoelectric command signals for prosthetic limbs and to generate electrotactile sensations to restore a sense of touch from prosthetic hands.

B) Number of Channels

The number of different muscles that may be controlled prosthetically to perform a given task is highly dependent on the nature of the task and the number of muscles still under voluntary control of the operator. The total number of muscles that operate the arm and hand can be in the order of 30-50, depending on how much of the scapular and shoulder motion is included and whether the intrinsic muscles of the hand are included. Some clinical applications of FES may require only a few channels, such as to open or close the whole hand around a large object (so-called palmar grasp). The upper limit seems more likely to be set by considerations of cost-benefit. Each BION2 implant may have several cost factors not limited to a cost for the device itself, its implantation, and the fitting time required to integrate it into a control algorithm. However, in the exemplary embodiments discussed below the applications may be limited to 20 simultaneously active implants.

C) Fault Tolerance

The biological sensorimotor control system is actually quite noisy, with many stochastic processes involved in the transmission and integration of all-or-none action potentials over a small dynamic range of possible frequencies (typically 5-300 pulses per second, pps). The natural redundancy of biological sensors and actuators, the low-pass properties of muscle and the inertial properties of the limb all tend to smooth out this noise. Furthermore, humans are adept at learning behavioral tactics that minimize its consequences for the performance of individual tasks. This suggested that the requirement for fault tolerance could be expressed more usefully in terms of functional consequences for the task at hand rather than bit-error rates and detection and correction levels.

III) System Design

We now discuss the main features of the designed system that fulfills the functional requirements for recovering functional movement are presented.

A) Patient Intention

The electromyogram (EMG) is a stochastic pattern of electrical potentials (typically on the order of 100-1000 $\mu V$ @ 100-3000 Hz when recorded from within a muscle) that arises from the temporospatial overlap of asynchronously firing motor units (see Cameron T, Loeb G E, et all "Micromodular implants to provide electrical stimulation of paralyzed muscles and limbs", IEEE Trans Biomed Eng 1997; 44: 781-790). If the patient has a paralyzed limb but there is some residual voluntary control of some muscles, the modulation envelope of their EMG signals can be used to infer the patient's intentions and control the electrical stimulation of the paralyzed muscles. The stimulating electrodes already present on the BION can be used to pick up the EMG potentials provided they are disconnected from the stimulus generation circuitry and the first stage amplifier blocks any polarization potentials on the electrodes.

The EMG signal has a modest signal-to-noise ratio (<40 dB) but wide dynamic range. Because of its stochastic nature, any assessment of its amplitude may require integration over as many samples as possible. The EMG sensing scheme that is included in BION2 may be based on digitizing the difference in amplitude between successive samples at a rate appropriate for the bandwidth (6 kS/s) and integrating the absolute value of those differences for a period of 10-50 ms that can be determined dynamically by the external controller (see frame architecture description below). A 10-bit analog-to-digital converter (ADC) and a 16-bit accumulator have been chosen to meet these demands.

B) Stimulus Control

As noted above, it may be desirable to have fine control of the percentage of the muscle that is recruited. The threshold and slope of electrical recruitment can vary widely depending on placement of the implanted stimulator. The strength of a stimulus pulse may depend on its charge, the product of pulse current and pulse duration. We have chosen in an exemplary embodiment to control the pulse current over a wide but coarse range consisting of powers of two (0.5, 1, 2, 4, 8, 16 and 32 mA). Pulse duration in each of these ranges may be controlled finely over the range 2 to 8000 µs by counting the internal clock extracted from the incoming 480 kHz RF carrier frequency for power and data.

Also as noted above, the usual firing rates for motor units may be relatively low (20-30 pps) in order to achieve reasonably smooth and minimally fatiguing contractions. But it may be desirable occasionally to provide bursts at much higher frequencies in order to achieve rapid and/or strong contractions or to produce electrotactile sensory percepts. This can be accommodated by the frame architecture described below, which provides a mechanism to generate duplicate or triplicate stimulus pulses with identical parameters within a given frame. Embodiments may also reduce force ripple at low stimulation rates by staggering the stimulus pulses from synergistic sites at different times within each frame.

C) Muscle Response

An exemplary embodiment may be able to measure the relative recruitment of the muscle in response to each stimulus pulse. This can be used during implantation to help direct a new implant into a site with a low threshold, to map a range of stimulus intensities to a percentage activation of the muscle, and to adjust stimulation parameters on-line to cope with shifts of this recruitment curve due to mechanical deformation of the contracting muscle. The same EMG recording and integration subsystem described above can be used for this task and the sampling time may be controlled and synchronized with the stimulation pulse. The embodiment may also avoid sampling the initial stimulus artifact and to sample only the so-called M-wave reflecting the immediate response of the activated muscle fibers (typically 1-5 ms window after the stimulus pulse).

D) Posture Sensing

In order to plan and coordinate movements and compensate for perturbations, the controller may need information about the starting posture and ongoing trajectory of these movements. We have developed three separate sensing modalities that are related to this information but with complementary strengths and weaknesses:

1) The inductive coil inside each BION implant can be used as an antenna to detect reference magnetic fields created outside the body such as by orthogonal coils mounted in a wheelchair. We have developed mathematical techniques to extract absolute position and orientation of a limb segment from such measurements obtained by two or more implants in that segment (see Tan W and Loeb G E, "Feasibility of prosthetic posture sensing via injectable electronic modules", IEEE Trans. Neural Systems & Rehab. Engng., in press). This might require up to eight 10-bit samples per implant per frame.

2) The orientation with respect to gravity and translational acceleration can be determined by a MEMS accelerometer which has 2 axes of piezoresistive bridge elements (see Zou Q, Tan W et al, "*Single-axis and Tri-axis Piezoelectric Bimorph Accelerometer*", IEEE/ASME Journal of Microelectromechanical Systems, in press). This would require two 10-bit samples per implant per frame.

3) The posture of distal joints of the hand and fingers can be determined without implanting devices in these sites, where they would be difficult to power. Instead, it can be inferred from changes in the relative position of implants in the muscles that operate those joints, much as the biological system infers those joint angles from the spindle stretch sensors in these muscles in the forearm (see Sachs N A and Loeb, G E, "Development of a BIONic muscle spindle for prosthetic proprioception", IEEE Trans. Biomedical Engineering, in press) (hence the name BIONic Spindle™.). Brief electrical pulses (<10 µs) generated by the stimulus pulse circuitry create potential gradients that spread by volume conduction throughout the limb (so-called stimulus artifact) but are ineffective at stimulating motor units. The EMG recording function of other implants may be synchronized with these brief stimulus pulses so that they measure the differences between the voltage at the height of the artifact and the baseline potentials on either side. Each implant can function as an emitter while some or all of the other implants act as detectors, producing a rich set of coupling values from which to infer complex hand postures. In an exemplary embodiment we anticipate using up to eight implants as emitters with each frame resulting in up to eight 10-bit samples per implant per frame.

The communication scheme that is presented next is intended to support all of these sensing functions and the substantial numbers of samples that each might need to collect, hold and transmit each frame. The first version BION2 may incorporate only the BIONic Spindle, so the description here provides details only for this posture sensing method and the EMG sensing functions described above.

IV) Communication Protocol

There are several systems designed for neuromuscular stimulation that include wireless RF powered microstimulators. In Gudnason G, Bruun E ("A chip for an implantable neural stimulator", Analog Integrated Circuits and Signal processing 22 (1999), 81-89, and Dong M), and Zhang C et all ("A wideband frequency-shift keying demodulator for wireless neural stimulation Microsystems", Journal of Zheijiang University SCIENCE A, 2006 7 (6): 1056-1060), unidirectional communication may provide stimulation parameters but there is no bidirectional communication to receive a feedback to control the movement.

Other systems, like the ones included in Lee S Y, Lee S C ("An implantable wireless bidirecional communication microstimulator for neuromuscular stimulation", IEEE Transactions on circuits and systems, vol 52, December 2005), Suaning G J, Lovell N H, ("CMOS neurostimulation ASIC with 100 channels, scaleable output and Bidirectional Radio-Frequency Telemetry", IEEE Transactions on Biomedical Engineering, vol 48, February 2001, pp 248-260), and Liu W, Vichienchom K et all ("A Neuro_Stimulus Chip with Telemetry Unit for Retinal Prosthetic Device", IEEE Journal of Solid-State Circuits, vol 35 Oct. 2000, pp 1487-1497) may be designed for a single implant application as cochlear implants or retinal prostheses so they don't present multiple control or implant synchronization issues. Some of them do not have demanding bandwidth requirements, for example Lee et al. uses the same frequency for forward and reverse telemetry from a single implant and Suaning et al. uses system reinitialization with every stimulus as the security mechanism to avoid errors in stimulation parameters.

The communication protocol for the BION system of the exemplary embodiment is configured to control up to 20 implants in real time. BIONs provide a platform for multiple applications and the protocol may provide reconfiguration of similar implants to perform very different tasks with different sensorimotor control requirements. The RF powering scheme can poses additional requirements to respond gracefully and rapidly to loss of configurational data stored in volatile RAM if and when individual implants move to a position where their received power drops below a critical level. Most of these aspects may require a selection of a communication protocol based on a sequence of frames, each of which consists of the same number and length of messages and the same order of actions.

A) Efficient Use of Forward & Reverse Data Rate

BIONs can be used for a wide range of clinical applications in which different numbers of implants will be used with widely varying requirements for sensing, stimulation and reaction speed. The main objective of the communication protocol was to allow the limited bit rate in each direction to be configured as needed for such applications. This configuration occurs during an initialization transmission to each implant, which sets the number of bits and the data that they represent for both forward and reverse telemetry during a given operational session.

1) Duplex Communication:

In the exemplary embodiment the physical layer is designed to allow full duplex communication with different codification schema and higher data rate for reverse telemetry because of the larger amount of sensory data expected for most applications. Forward telemetry in BION1 is via a frequency-shift keyed (FSK) signal over a 480 kHz carrier frequency that provides the clock and power for all implants. The data are Manchester-encoded with 2 carrier cycles per state and 2 Manchester-encoded states per bit, resulting in 120 kb/s transmission. The reverse telemetry capability is added in BION2 via an on-off keyed (OOK) bursts of a crystal-stabilized 400 MHz carrier whose bandwidth is limited by the boundaries of a single channel in Medical Implant Communications Service (MICS) band (see Falcon C, "Inside implantable Devices", Medical Design Technology, October 2004 and Sivard A, Bradley P et al, "Challenges of in-body communications", Embedded Systems Europe, March 2005 pp 34-37). Each bit may occupy one cycle of the 480 kHz master clock, with the presence and absence of carrier signifying ones and zeros, respectively. Each reverse telemetry transmission arises in turn from a separate implant, which may preface the actual data with a short, fixed header of ones and zeros to allow the external receiver to determine the appropriate detection threshold.

Figure 2:
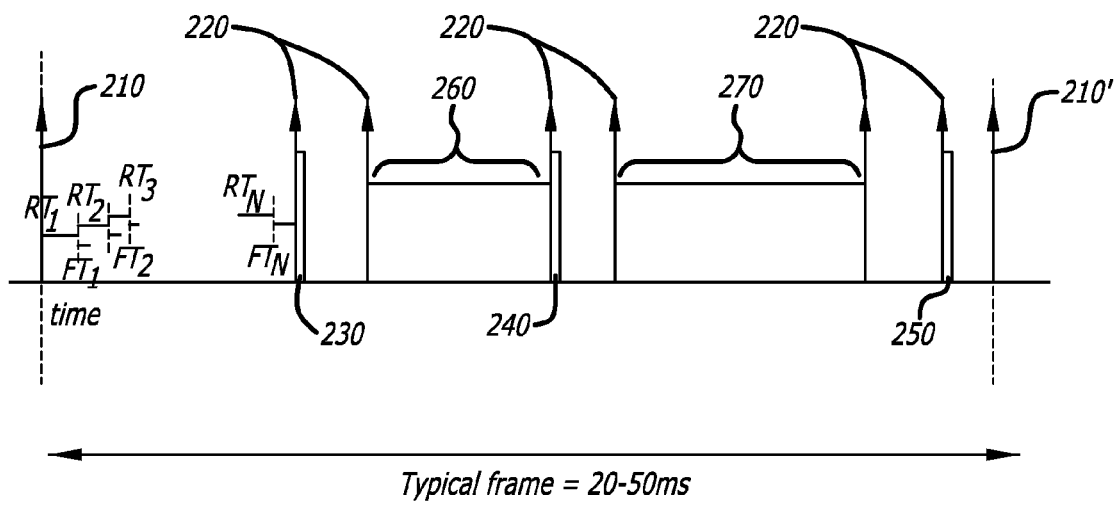
FIG. 2 illustrates an exemplary control signals in a microstimulator frame.

2) Prefixed Time Slots:

The time slots to define the forward and reverse transmissions for each implant may be fixed by the external controller when the system is turned on and the implants are initialized (FIG. 2). The use of these predefined channels may have few advantages: first, the collisions between transmissions from several BION implants sending data to the controller simultaneously are avoided. In addition, the controller can identify data from each BION without including extensive headers in back telemetry and each BION can identify the presence of incoming data from the controller also without headers in forward telemetry. All devices and actions may be synchronized by counting clock cycles based on the inward telemetry and power carrier transmitted by the external controller.

B) Predictable Frame Intervals for Reflex Adjustment

Each frame is a programmed sequence of events that are performed by all implants that may repeat at a rate consistent with the default stimulation frequency for each muscle (typically 20-30 pps) or an integer multiple thereof. The minimal delay for responding to any sensory feedback or command signal can be two frames. Sensory transduction occurs in one frame to assemble the data sent by reverse telemetry in the next frame, and then the controller computes the desired response and transmits it at the beginning of the third frame for execution during the remainder of that frame. The duration of a frame and the exact timing of events within the frame can be controlled by two types of Sync signals that are encoded by special inward telemetry transmissions as violations of Manchester coding that cannot arise from the data sequences themselves.

A Frame Sync 210 in FIG. 2 is a signal that triggers a new sequence of actions. In this exemplary embodiment the of the protocol a frame is defined as the period between two Frame Syncs 210 and 210' and the frame time is set by the external controller in real time.

Internal Syncs 220 are signals that can be received at any time inside each frame. These signals may be responsible for triggering each action in the frame (e.g. stimulation, starting and ending points of sensing modalities and reinitialization if necessary) in an order that is programmed as part of the initialization transmission.

The exemplary embodiment of frame Sync and Internal Sync concepts are illustrated in FIG. 2 by the sequence of events included in a frame and their respective timing. The first event after a Frame Sync 210 is the communication stage: reverse and forward telemetry from and to each implant, respectively, according to bit counts and time slots that are programmed as part of the initialization of each implant. After the communication stage, the BIONs wait for the Internal Syncs that are used to trigger various events during the frame.

The BION example included in FIG. 2 stimulates the muscle at 230, measures the muscle response by integrating the M-wave for a variable period 260, M-wave detecting stops and spindle window is triggered 240, detects the joint position by measuring spindle pulses from other implants for the period 270, and finally integrates the background EMG activity over a variable period to provide voluntary command data. All sensor data gathered during these functions are held in a LIFO register until the next frame, when its reverse telemetry slot arrives and it sends the data back to the controller.

One of the initialization registers is called "Sync Mask" because it determines which BION action (i.e. stimulation or various sensing modes) is triggered by each successive Internal Sync signal. The combination of Frame Syncs, Internal Syncs and Sync Masks makes the control inside a frame very flexible while permitting tight synchronization of events between implants (e.g. having one implant sense the response to stimuli generated by another implant):

Improving sensing modality accuracy and dynamic range: the integration time of two sensing modalities (EMG and M-wave) may be controlled from the outside with Internal Syncs to start and stop the measuring period. M-wave measures the muscle response to a stimulus pulse from the same or a different implant. It may vary in latency and duration from muscle to muscle. EMG records the residual voluntary control of the muscle. Accuracy may be improved by integrating for as long as possible. By starting and stopping these digital integrators according to the Internal Syncs, the external controller can adjust them dynamically without requiring transmission and storage of these timing parameters.

Increasing the strength of muscle contraction: one powerful and rapid way to increase the effectiveness of muscle stimulation is to stimulate twice within a normal frame, making use of the "catch property" that arises from the calcium kinetics in the muscle fibers. This can be done using Internal Syncs to trigger this "extra stimulus pulse" in some selected BION implants. According to FIG. 2, the last Internal Sync is sent by the controller only when an additional stimulation pulse is required. Thus, this provides a simple way to change between single and double stimulation 250 that can be controlled frame by frame.

Smoothing limb movements: in order to produce smooth joint torques, the physiological activity of motor units tends to be asynchronous. To emulate this effect it may be desirable to stimulate synergistic muscles at different times in each frame. This may be another feature that can be achieved by strategically phasing Sync Mask values for stimulation, as shown in FIG. 3.

Figure 3:
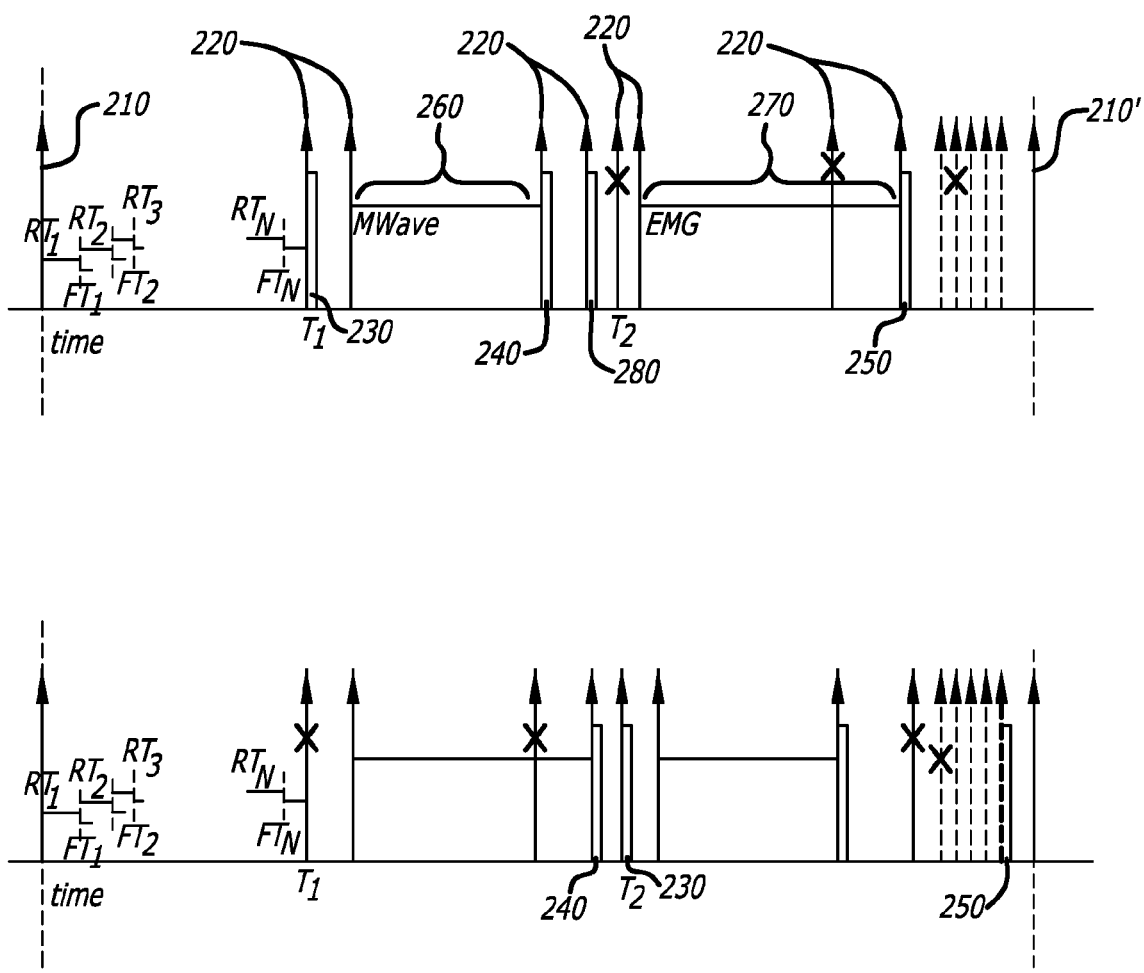
FIG. 3 illustrates control signals in a microstimulator frame for two different sets of microstimulator to obtain a smooth joint torque.

In FIG. 3, the Internal Sync signals that are not used for the corresponding BION are marked with an X and the optional ones are represented as broken lines. In this particular case, some of the BION implants in the system are stimulating the muscles at time T1 and some of them at T2. After stimulation, each implant records the M-wave response. In the case shown, to obtain double rate stimulation additional Internal Syncs can be sent, and the double stimulation rate is achieved with the 8th Internal Sync for the first BION and with the 13th for the second one.

C) Error Tolerance by Limiting Consequences

The system communication errors can be classified into critical errors and bearable errors depending on the potential consequences. Bearable errors are errors in dynamic data transmission whose possible range may be limited to "safe values" with "dynamic mask" mechanism discussed in this section. Critical errors in BION communication that can be avoided are those whose consequences are indeterminate such as sending commands to the wrong implant.

To avoid errors in BION identification, initialization commands are preceded with the unique 32-bit ID code that is hard-wired into each implant ASIC as Read-Only Memory, similar to the ROM used in radio frequency identification (RFID) transponders. This can include the critical timing information for the forward and reverse telemetry slots during the communication phase of each frame. To avoid critical errors in BION initialization, each BION echoes the whole initialization sequence of parameters, bit by bit, back to the controller.

Figure 4:
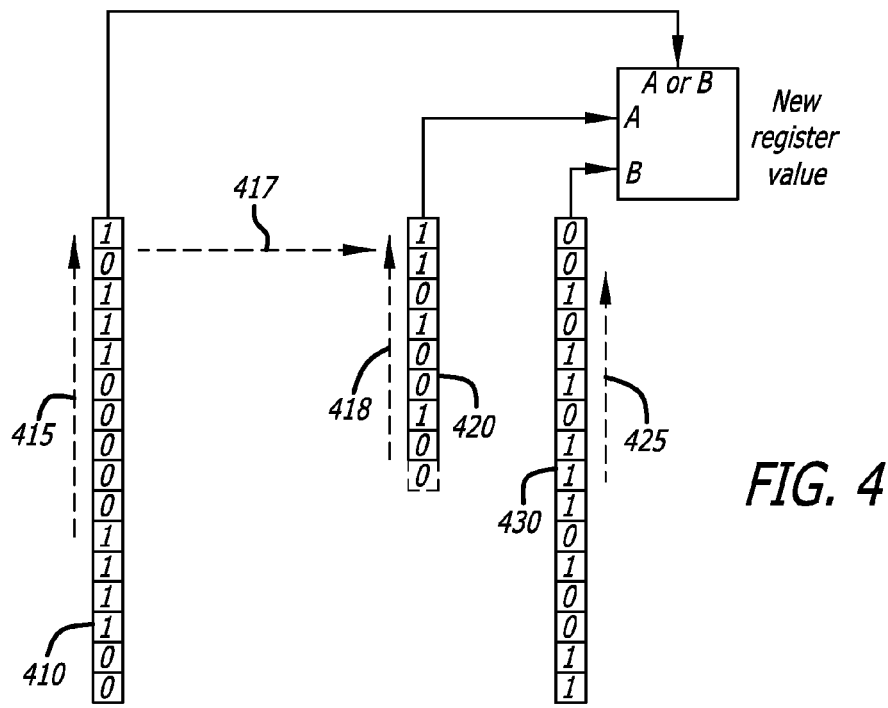
FIG. 4 illustrates an exemplary dynamic mask operation.

To ensure that the maximal stimulation error caused by communication errors in the dynamic parameters are bearable and will never be dangerous for the patient, the "Dynamic Mask" mechanism can be used (FIG. 4). The Dynamic Mask is a register (410) included in each BION whose bits correspond to each bit stored in the parameter registers for stimulation and sensing modalities. The bits shift with every clock in the direction of arrow 415. If a bit in the parameter registers is to be affected by dynamic data on a frame-by-frame basis, its corresponding bit in the dynamic mask register is set to a "1"; if that value is to remain unchanged, its corresponding bit in the dynamic mask register is set to a "0", essentially protecting that bit to stay at the value initially set in the parameter or BION registers 430. The buffer 420 shifts in the direction of the arrow 418 when a "1" is received from the mask register 410. The bits in the BION registers 430 shift in the direction of the arrow 425 with every clock.

In order to confirm the validity of the communications protocol, a software simulator has been developed. The simulator consists of two modules, a module to simulate the external controller function and a module to simulate the BION module. The two modules are combined to operate a system with one controller and up to 20 implants. The Dynamic Mask thus can be used to specify which bits of any parameter of any stimulus or sensing modality are to be changeable and "dynamic" during normal operation (FIG. 4).

The dynamic mask has two purposes: one to avoid dangerous errors and to allow frequently changing parameters to be adjusted while minimizing the number of bits sent in each frame. One example of how this might be used is to set the dynamic range of possible stimulation values to cover only the values from threshold to saturation for each muscle. The coarse control of stimulus current (n steps of 2n) could be set at one value (e.g. 4 mA) and the central five bits of stimulus duration (12 bit counter with 2 μs clock) would be enabled by the Dynamic Mask so that the only possible stimulus durations would be 16-496 us in 16 us steps. Bearable errors in dynamic parameters are detected with a single parity bit (50% probability) in order to report the occurrence of received errors to the controller during the reverse telemetry phase of the next frame. Because the possible errors have been limited to a safe range by the Dynamic Mask, it may be better for the BION to act with the wrong parameters than to skip stimulation and allow the muscle to relax.

D) Dynamic Reinitialization of Individual Implants

All of the programmable parameters of an implant (including the critical communication timing and mask registers described above) can be held in volatile registers that depend on power received by inductive coupling from the external coil-driver. The very movement created by the muscle stimulation can cause shifts in the relative alignment between the coil-driver and one or more implants. If the received voltage in a given implant drops under a critical level, that implant goes through a reset operation, clearing all internal registers. Upon the return of sufficient power, this implant no longer participates in the normal communication phase of any ongoing frames unless and until it is completely reinitialized. The absence of any detectable reverse telemetry carrier during the pre-assigned time slot for this implant informs the external controller which implant needs reinitialization. In the event of the occasional and isolated drop-outs, the dynamic reinitialization of individual implants is provided without affecting the ongoing performance of the other implants.

Figure 5:
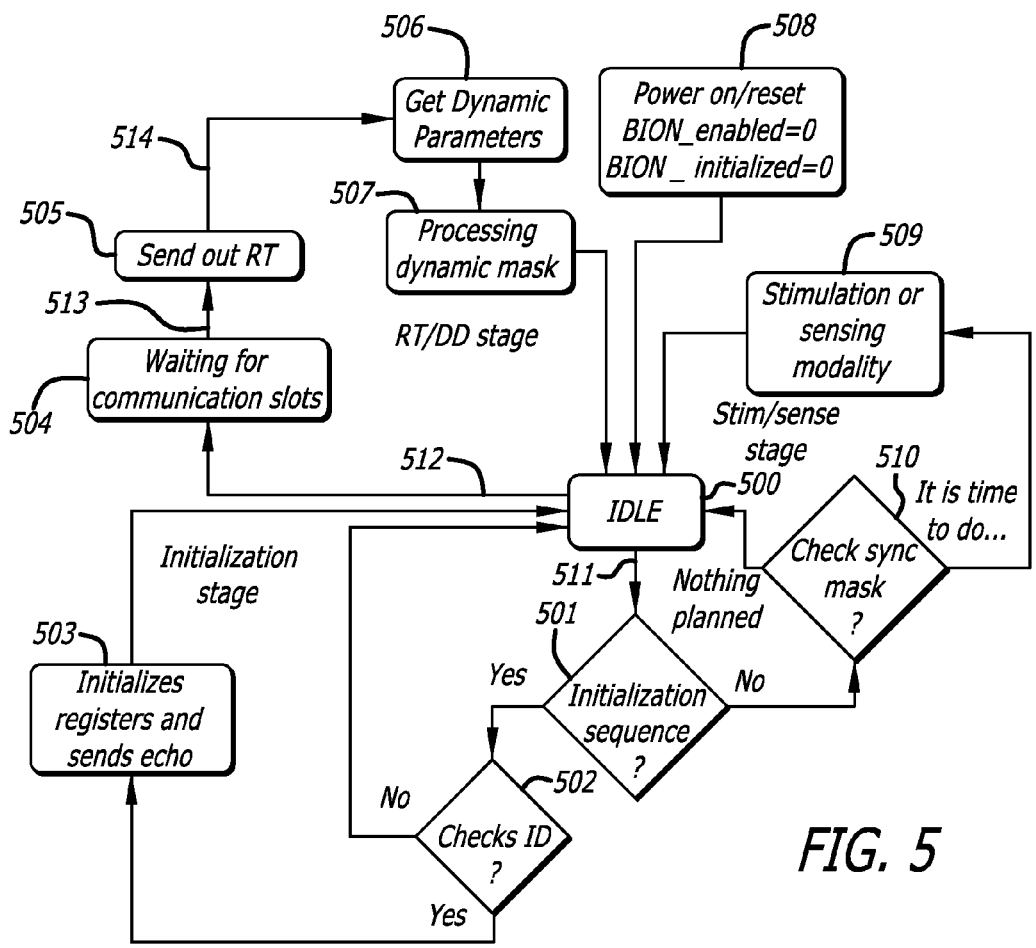
FIG. 5 is a schematic of microstimulator state diagram.

The programming steps of the BION during an operation is depicted in the block diagram of FIG. 5. Any implant that is in an uninitialized state will be effectively idling 500 and will respond only to a special initialization code consisting of an Internal Sync 511 followed by a bit value indicating that the subsequent data constitute an initialization sequence.

Upon receiving the Internal Sync 511, BION checks for initialization sequence 501. The first part of the initialization sequence must be the complete 32 bit ID code of the implant in question. At step 502, the BION checks for the ID code, If the ID code matches the ID code in the ASIC ROM, the subsequent data are used to initialize all programmable registers at step 503 and the whole initialization sequence will be echoed via reverse telemetry to external controller for complete verification. The implant is now initialized but not yet enabled and in idle 500. The enablement occurs only in the next frame by receiving Frame Sync 512 from the external controller, when the external controller detects its reverse telemetry signal at 505 in the predetermined correct time-slot 513 and transmits the first set of dynamic command data 516 in its given predetermined forward telemetry slot 514. The dynamic parameters may be processed by the dynamic mask 507 as discussed above. Receiving the next Internal Sync at 511 the initialized BION checks to see if the parameters are initialization sequence, if not, at step 510 the BIOn checks for the action to be performed by the Internal Sync. If it decides that a stimulation or sensing needs to be performed, the program proceeds to step 509 to do one or the other.

Thus the state diagram in FIG. 5 can be divided into three stages: initialization, communication and stimulation/sensing. The controller can reinitialize any device at any time that the device is in the "Idle" state, i.e. not transmitting or receiving data. This can be useful to allow changes in parameters that are outside the previous dynamic range (e.g. the stimulus current in the example above could be shifted from 4 mA to 8 mA).

V) Stimulation and Performance

In order to confirm the validity of the communications protocol, a software simulator has been developed. The simulator consists of two modules, a module to simulate the external controller function and a BION module, that are combined to generate a system with one controller and up to 20 implants.

Figure 6A:
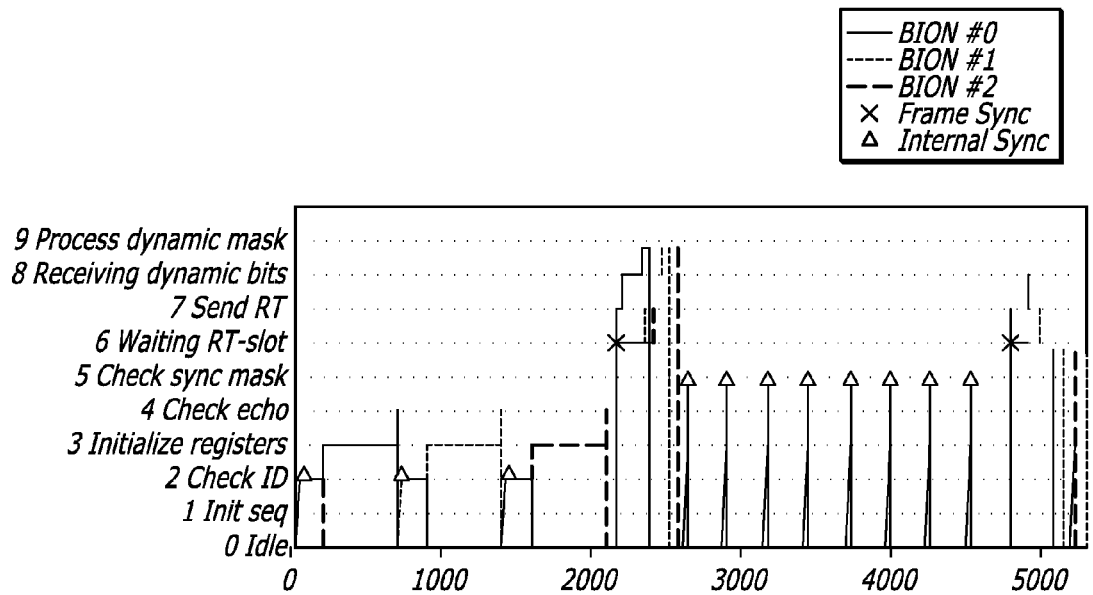
FIGS. 6A-B illustrates simulation of a microstimulator system composed of 3 implants 6A) sequence of events to initialize the system and first frame and 6B) Reverse Telemetry echo during initialization stage and data after the first frame.
Figure 6B:
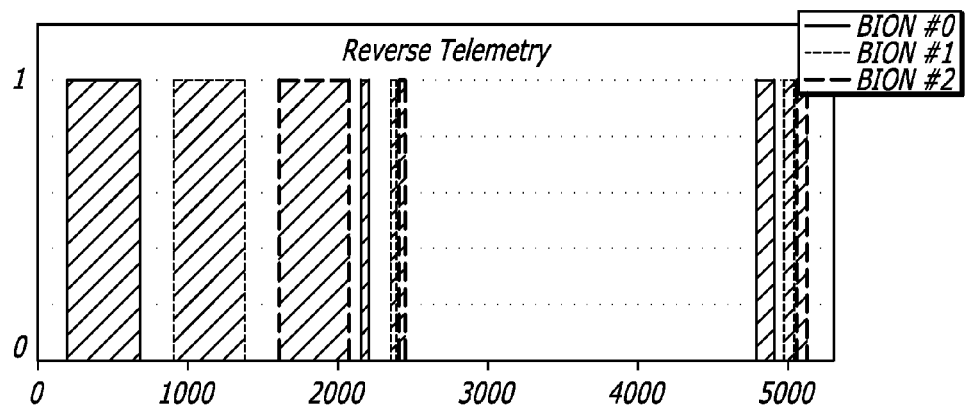
Figure 7A:
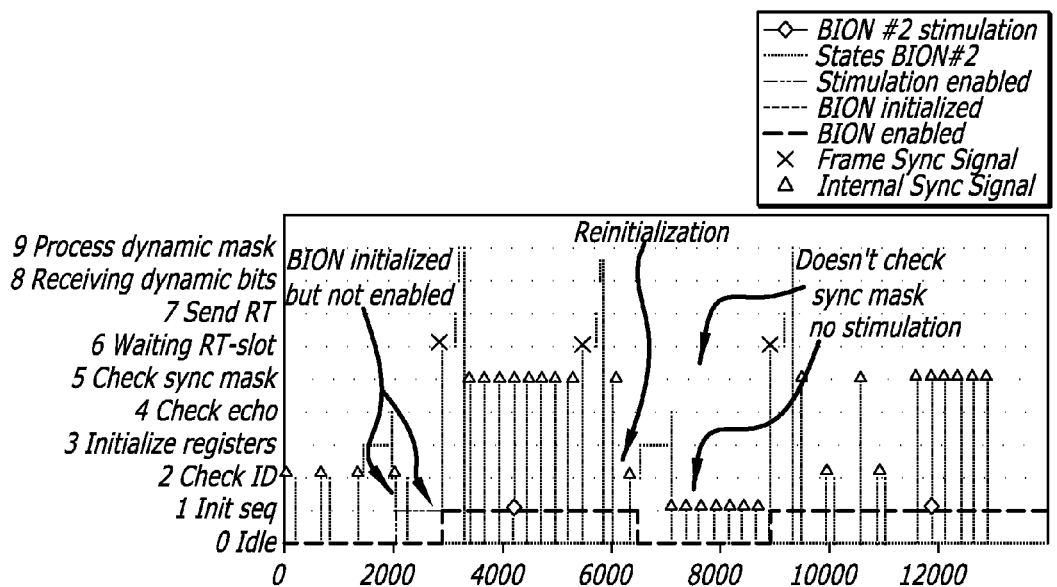
FIG. 7A-B illustrates stimulation of a BION system composed by 4 implants BION #2 performance A) Reinitialization of a single implant in second internal sync signal. B) Reinitialization of other implants doesn't affect performance of this BION.
Figure 7B:
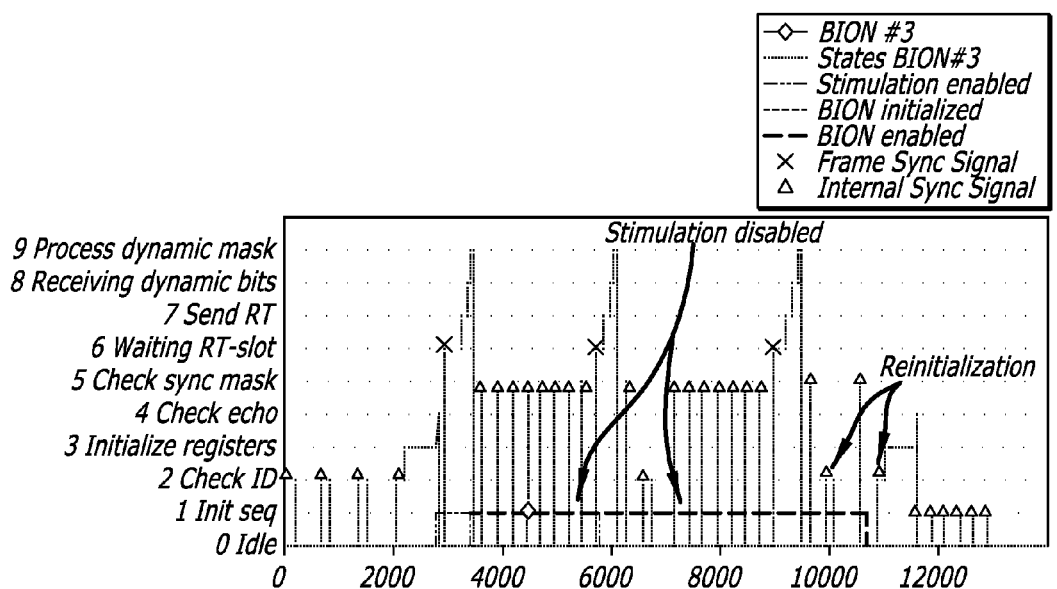

The input of the controller module is a high level sequence of parameters used to initialize the BIONs and control the system through several subsequent frames, and the output is the sequence of bits that will be sent to each BION along with the times these sequences are to be sent. Each simulated BION node is represented by the BION module, and receives the sequence of bits, responds according to the protocol and generates an output file that includes the sequence of states of the implant. Each output file records the contents of each register in the BION, the reverse telemetry data output and the states of the signals to activate the different sensing modalities. FIGS. 6 and 7 show the graphical representation of the simulator output for a complete system and for individual implants respectively. FIG. 6(*a*) shows the sequence of events for each one of three BION implants in the system. Each BION starts in the idle state and checks the initialization sequence and the ID sent, but only the implant whose ID matches with the ID sent by the controller initializes its registers and sends the echoed data to the controller. This will ensure that the sequence sent was properly received by the BION. After initializing all the implants, the external controller sends a Frame Sync and the three implants wait for their designated RT slot, send the reverse telemetry data, receive new dynamic bits and then process the dynamic data. The simulation demonstrates that there is no overlap between RT transmissions from different implants and that each one of the implants receives its new parameters and updates its registers correctly. Once all implants have their dynamic data processed, the external controller sends a series of internal syncs. With each internal sync, all implants simultaneously check their sync masks to identify the action that each should perform. The data sent back from the implants are illustrated in FIG. 6(*b*). During initialization, initialization data is echoed back to the external controller as it is received, and during each frame, sensory data are sent during "send RT" state.

FIG. 7 depicts a system having 4 implants from the perspective of an individual implant. FIG. 7(*a*) includes the internal register values for BION#2. In the sequence of events it is seen that this BION is initialized with the third initialization sequence, which is when this particular implant recognizes its own ID. Upon its initialization, the implant activates its "BION initialized" flag. Then the first frame starts, in which the implant receives a frame sync signal and immediately the "BION enabled" flag is activated. The BION then waits for its designated RT slot, when it sends RT, receives the new dynamic bits, processes those dynamic bits and activates the "Stimulation enabled" flag. When the stimulation has been activated, BION#2 stimulates upon the proper internal sync, depending on its "Stimulation sync mask" register.

In the example illustrated in FIG. 7(*a*) stimulation will correspond to the 4th internal sync signal. When the next frame sync is received the "Stimulation enabled" flag is deactivated until the new dynamic parameters have been processed. But in this example, in the second frame the external controller will reinitialize this BION. Thus, at the second internal sync the external controller includes an initialization sequence followed by BION#2 ID and the complete set of initialization parameters. This BION is deactivated in this frame with respect to stimulation and sensing and will be enabled again in the next frame. FIG. 7(*b*) includes the same system but from the point of view of BION#3, which is not affected by the BION#2 reinitialization sequence and which, in this case, has its stimulation disabled in the second frame through the dynamic data sent to it by the external controller in that frame.

In addition to confirming the correct and robust operation of the communication protocol under a range of command sequences and conditions, the software simulation serves two additional purposes. First, the simulation programs can be used to generate and validate the digital logic blocks for the actual hardware, which will be ultimately compiled into silicon for the implant ASIC and programmed into an FPGA for the external controller. Second, it generates valid input and corresponding output files to be compared with the performance of actual hardware during the testing phase.

The BION2 implant requires 32 bits of ID code plus 137 bits of initialization data for fixed parameters, dynamic mask and control bits. One such BION is initialized in 1.14 ms, and a system with 20 BIONs can be initialized in 22.8 ms. The maximal duration of the reverse telemetry depends on the length of the LIFO register, presently set to 72 bits but likely to be extended as new sensory modalities become available in future models. The longest duration of the reverse telemetry from 20 such implants would be about 3 ms (with all or most of the forward command data to one implant occurring during the reverse-telemetry period of the next implant). If the frame duration is set at 20 ms, most of the frame time will be available for stimulating and sensing, with only about 15% required for communication purposes and processing overhead. Such a frame rate would enable continuous adjustment of stimulus parameters at 50 Hz, which is about twice the usual firing rate for human muscle fibers. Even higher stimulus rates could be achieved using the repetitive stimulus train capabilities enabled by the Sync Mask.

Figure 8:
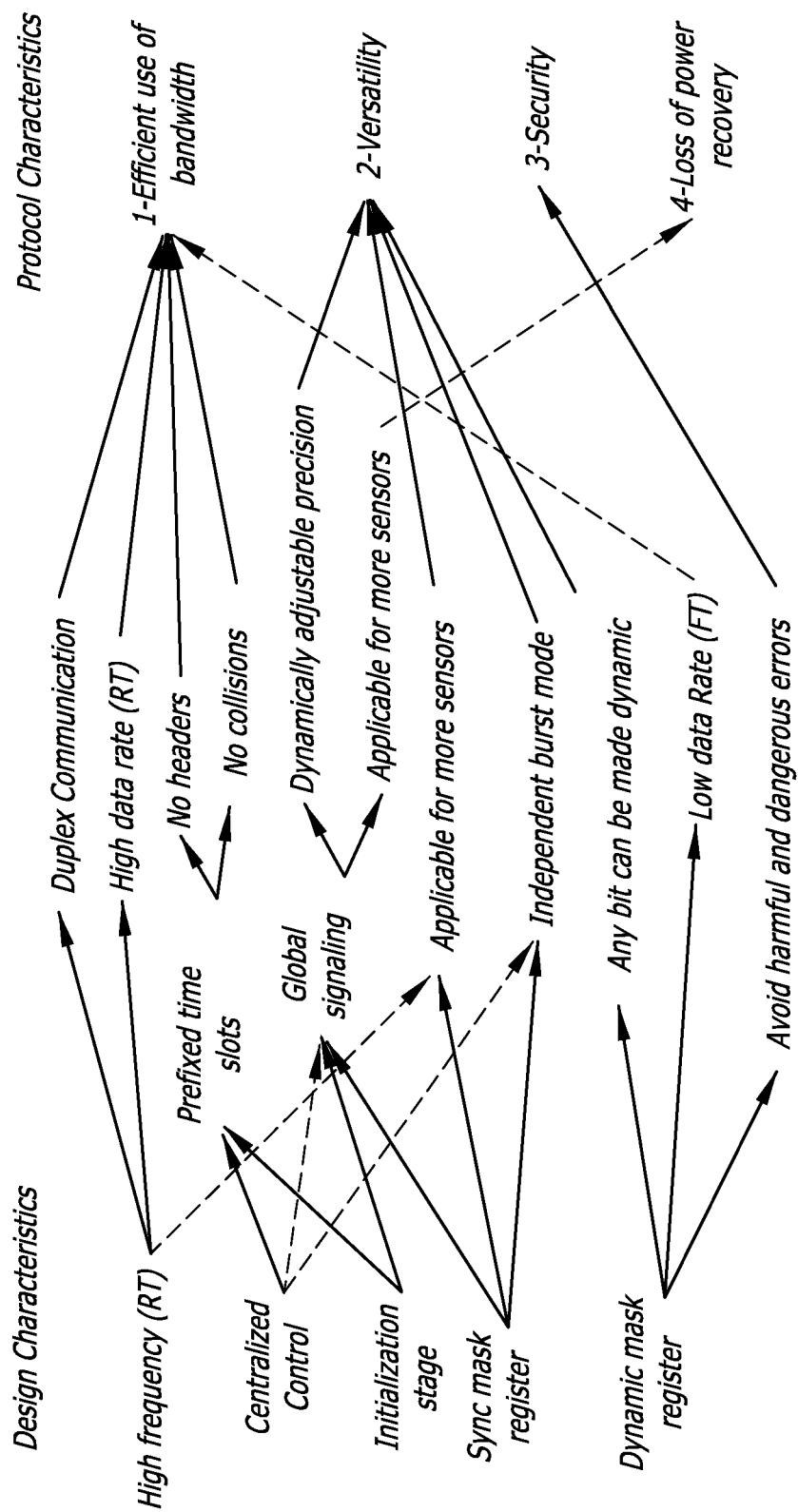
FIG. 8 is a schematic of summary of protocol characteristics.

The communication protocol disclosed incorporates several strategies useful in systems in which multiple devices with a range of possible functions must be configured dynamically to work with command and data channels that have limited bit rates and non-zero bit error rates. A summary of the system characteristics used in BION2 implementation is presented in FIG. 8 to illustrate how this system implementation makes possible the fulfillment of the clinical requirements. The global signals Frame Sync and Internal Sync and the run-time assignment of bit slots for inward and outward full-duplex telemetry for each device greatly reduces time normally allocated to headers and device addresses in reconfigurable systems. In addition, the Dynamic Mask disclosed allows the controller to select specific parts of sensing and stimulating parameters for dynamic adjustment, while protecting the system from gross error. This enables aggressive use of the available carrier bandwidth to achieve high data rates without requiring complex and time-consuming error correction.

The following articles contain information that may be used in various embodiments of the Flexible Communication and Control Protocol for a Wireless Sensor/Mirostimulator Network, and all of their contents are incorporated herein by reference: Cameron T, Loeb G E, et all "*Micromodular implants to provide electrical stimulation of paralyzed muscles and limbs*", IEEE Trans Biomed Eng 1997; 44: 781-790; Dupont Salter A C, Bagg S D et al, "First clinical experience with BION implants for therapeutic electrical stimulation", Neuromodulation 7, 2004, pp 38-47; Loeb G E, Richmond F J R et al, "*BION Injectable Interfaces with Peripheral Nerves and Muscles*", Neurosurgical Focus, Vol 20:1-9, May 2006; Zou Q, Tan W et al, "*Single-axis and Tri-axis Piezoelectric Bimorph Accelerometer*", IEEE/ASME Journal of Microelectromechanical Systems, in press; Tan W and Loeb G E, "Feasibility of prosthetic posture sensing via injectable electronic modules", IEEE Trans. Neural Systems & Rehab. Engng., in press; Sachs N A and Loeb, G E, "Development of a BIONic muscle spindle for prosthetic proprioception", IEEE Trans. Biomedical Engineering, in press; Kaliki R R, Davoodi R et al, "*The Effects of Training Set on Prediction of Elbow Trajectory from Shoulder Trajectory during Reaching to Targets*", 28$^{th}$ Annual International Conference IEEE Engineering in Medicine and Biological Society (EMBS), pp 5483-5486; Gudnason G, Nielsen et al, "*A distributed transducer system for functional electrical stimulation*", Proc. ICECS, Malta, vol. 1, pp. 397-400, 2001; Loeb G E and Ghez C, "*The Motor Unit and Muscle Action*", Principles of Neural Science, 4$^{th}$ Ed Mc Graw Hill 2000, Chapter 34, pp 674-694; Gudnason G, Bruun E "*A chip for an implantable neural stimulator*", Analog Integrated Circuits and Signal processing 22 (1999), 81-89; Dong M, Zhang C et all "A wideband frequency-shift keying demodulator for wireless neural stimulation microsystems", Journal of Zheijiang University SCIENCE A, 2006 7 (6): 1056-1060; Lee S Y, Lee S C, "An implantable wireless bidirectional communication microstimulator for neuromuscular stimulation", IEEE Transactions on circuits and systems, vol 52, December 2005; Suaning G J, Lovell N H, "CMOS neurostimulation ASIC with 100 channels, scaleable output and Bidirectional Radio-Frequency; Telemetry", IEEE Transactions on Biomedical Engineering, vol 48, February 2001, pp 248-260; Liu W, Vichienchom K et al, "*A Neuro_Stimulus Chip with Telemetry Unit for Retinal Prosthetic Device*", IEEE Journal of Solid-State Circuits, vol 35 Oct. 2000, pp 1487-1497; Falcon C, "Inside implantable Devices", Medical Design Technology, October 2004; Sivard A, Bradley P et al, "*Challenges of in-body communications*", Embedded Systems Europe, March 2005 pp 34-37.

The previous description of the disclosed embodiments is provided to enable any person skilled in the art to make or use the microstimulator injection devices, methods and systems. Various modifications to these embodiments will be readily apparent to those skilled in the art, and the generic principles defined herein may be applied to other embodiments without departing from the spirit or scope of the devices, methods and systems described herein. Thus, the charge meter circuits, devices, methods and systems are not intended to be limited to the embodiments shown herein but are to be accorded the widest scope consistent with the principles and novel features disclosed herein.

The invention claimed is:

1. A microstimulator implant controller for restoring functional movement in one or more muscles of a patient's body, the controller comprising:
   a. a processor configured to receive input parameters, to initialize one or more implants that are installed within a patient's body with initialization data based on the input parameters, and to control various processes in the one or more implants by transmitting dynamic data,
      wherein the initialization data include a unique identification data for each of the one or more implants and data required to enable the one or more implants to perform one or more actions,
      wherein the initialization data further include data defining a sequence of actions to be performed by the one or more implants in a frame; and
      wherein the actions include stimulation of one or more muscles within the patient's body;
   b. a transmitter configured to transmit the initialization data to the one or more implants by forward telemetry transmission;
      wherein the transmitter is further configured to transmit a frame sync signal to the one or more implants in order to trigger a start of a new frame;
      wherein the transmitter is further configured to transmit one or more internal sync signals to the one or more implants after the frame sync signal is transmitted in order to trigger one or more actions to be performed by the one or more implants according to the initialization data defining a sequence of actions in the frame; and
   c. a receiver configured to receive back the transmitted initialization data from the one or more implants by reverse telemetry transmission, wherein the receiving back the transmitted initialization data is an indication to the processor that the initialization data has been received accordingly by the one or more implants;
      wherein the receiver is further configured to receive M-waves measured by the one or more implants in response to the muscle stimulation; and
      wherein the receiver is further configured to receive electromyogram (EMG) data detected by the one or more implants.

2. The controller of claim 1, wherein the transmitted initialization data further comprising predetermined time slots for the one or more implants' forward and reverse transmission so that collisions between the transmissions are avoided.

3. The controller of claim 2, wherein the processor is further configured to initialize up to 20 implants.

4. The controller of claim 1 wherein the received initialization data by the processor is an indication that the unique identification transmitted to the implant has been matched to a unique identification data that is stored in the implant.

5. The controller of claim 2, wherein the processor is further configured to reinitialize the one or more implants in the event of implants power dropping below a predetermined level.

6. The controller of claim 2, wherein the processor reinitializes the one or more implants when the reverse telemetry data has not been received within the predetermined time slot.

7. The controller of claim 1, wherein the forward telemetry is via a frequency-shift keyed (FSK) signal and wherein the data is Manchester-encoded.

8. The controller of claim 1, wherein the reverse telemetry received from the implant via an on-off keyed (OOK) bursts in the implant.

9. The controller of claim 1, wherein the processor is further configured to control frame duration and timing for the one or more internal Sync signals transmitted in each frame.

10. The controller of claim 9, wherein the processor is further configured to encode by Manchester violation the frame onset and the timing of the one or more internal Sync signals.

11. The controller of claim 1, wherein the receiver is configured to receive from one or more implants the electrical fields generated by one or more implants, wherein the generated electrical fields are the product of the implant delivering electrical current pulses.

12. The controller of claim 1, wherein the processor is further configured to dynamically adjust the stimulation data of the one or more implants based on the received data from the one or more implants.

13. The controller of claim 1, wherein the received EMG data corresponds to the patient's residual voluntary movement of a muscle.

14. The controller of claim 1, wherein the transmitted initialization data further include mask data in order to prevent changing of certain values in the one or more implants according to dynamic data received subsequently.

15. The controller of claim 14, wherein the mask data delimit the range of stimulation values by setting a bit in the register of the one or more implants to remain unchanged.

16. The controller of claim 1, wherein the receiver is further configured to receive positional data from the one or more of the implants.

17. The controller of claim 16, wherein based on the positional data the processor is further configured to derive the coordinates of the one or more implants relative to positions of a plurality of coils installed external to patient's body.

18. The controller of claim 16, wherein the positional data is gravitational data.

19. The controller of claim 1, wherein the receiver is further configured to receive the M-waves measured by the one or more implants in response to the muscle stimulation.

20. The controller of claim 19, wherein the processor is further configured to trigger a spindle window after detection of the M-waves stops.

21. The controller of claim 20, wherein the receiver is further configured to receive the electromyogram (EMG) data measured and integrated by the one or more implants after the spindle window is triggered.

22. The controller of claim 1, wherein the controller is further configured to stimulate the muscle twice after a new frame is started.

23. A microstimulator implant for restoring functional movement in muscle of a patient's body, the implant comprising:
   a) a memory unit configured to store a unique identification data assigned to the implant;
   b) a receiver configured to wirelessly receive initialization data from an external controller by forward telemetry, wherein the initialization data including a unique identification data and data required to program the implants registers with one or more actions;
   c) a processor configured to receive and process the received initialization data, wherein the processing including comparing of the received unique identification data with the stored identification data;
   d) a transmitter configured to transmit the received initializing data back to the external controller by telemetry if the received and the stored unique identification data match;
   e) a pair of electrodes configured to stimulate a muscle within the patient's body based on the programmed registers of the implant; wherein the electrodes are further configured to sense electromyogram (EMO) potentials corresponding to the patient's voluntary movement; and
   f) at least one sensor configured to detect signals from the stimulated muscle;
   and wherein the transmitter is further configured to transmit the data corresponding to the detected signals to the external controller; wherein the sensor is further configured to detect M-waves in response to muscle stimulation.

24. The implant of claim 23, wherein the registers are any one of LIFO register, programmable register, Sync Mask register, Dynamic register or stimulation parameter register.

25. The implant of claim 23, wherein the registers are configured to go through a reset operation in the event power dropping in the implant below a critical level.

26. The implant of claim 23, wherein the sensor is any one of electrical, magnetic or mechanical sensors.

27. The implant of claim 23, wherein the electrodes are further configured to send data by reverse telemetry.

28. The implant of claim 23, wherein the implant further comprising a sensor that is configured to sense electrical fields generated by one or more other implants.

29. The implant of claim 23, wherein the implant is further comprising a sensor that is configured to sense the implant's position.

30. The implant of claim 23, wherein the implant is further comprising a sensor that is configured to detect acceleration.

31. The implant of claim 23, wherein the initialization data further comprising predetermined time slots designated for the implants forward and reverse transmission so that collisions between the transmissions are avoided.

32. The implant of claim 31, wherein the implant is configured to be reinitialized when the reverse telemetry data has not been received within the predetermined time slot.

33. The implant of claim 27, wherein the reverse telemetry is via an on-off keyed (OOK) bursts in the implant.

34. The implant of claim 23, wherein the initialization data further include data defining a sequence of actions to be performed by the one or more implants in a frame.

35. The implant of claim 34, wherein the receiver is further configured to receive a frame sync signal from the external controller in order to trigger a start of a new frame.

36. The implant of claim 35, wherein the receiver is further configured to receive an internal sync signal from the external controller in order to trigger one or more actions to be performed by the implant within the frame.

37. The implant of claim 34, wherein the initialization data further include data corresponding to duration of the frame.

38. The implant of claim 36, wherein the received frame Sync and the Internal Sync are Manchester violation encoded.

39. The implant of claim 23, wherein the stimulation parameter is dynamically changed by the external controller.

40. The implant of claim 23, wherein the received initialization data further include mask data in order to prevent changing of certain values in the implant according to dynamic data received subsequently.

41. The implant of claim 40, wherein the mask data delimit the range of stimulation values by setting a bit in register of the implant to remain unchanged.

42. The implant of claim 23, wherein the implant further comprising a sensor that is configured to receive positional data from one or more other implants.

43. The implant of claim 42, wherein the positional data is gravitational data.

44. The implant of claim 23, wherein the processor is further configured to integrate the M-waves measured by the one or more implants in response to the muscle stimulation.

45. The implant of claim 44, wherein the processor is further configured to integrate the electromyogram (EMG) data measured by the one or more implants.

46. The implant of claim 23, wherein the electrodes are further configured to stimulate the muscle twice.

47. A neuromuscular implant system for restoring functional movement in one or more muscles of a patient's body, the system comprising:
  a) a control unit located external to the patient's body configured to initialize one or more implants with initialization data, transmitting the initialization data by forward telemetry to each of the one or more implants, wherein the initialization data include one or more muscle stimulation data, timing data, and a unique implant identification data; wherein the control unit is further configured to verify the proper receipt of the initialization data by the one or more implants by receiving the transmitted initialization data back from the one or more implants; wherein the control unit is further configured to receive M-waves measured by the one or more implants in response to the muscle stimulation: wherein the control unit is further configured to receive electromyogram (EMG) data detected by the one or more implants; and
  b) one or more implants having a stored unique identification data installed within the patient's body, configured to receive the initialization data and to electrically stimulate one or more muscles within the patient's body, to detect signals generated by the one or more stimulated muscles, and to send by reverse telemetry the detected signal to the external control unit.

48. The system of claim 47, wherein the one or more implants are configured to be initialized by the control unit prior to the stimulation of the one or more muscle.

49. The system of claim 47, wherein the one or more implants are further configured to match the sent identification code from the control unit with their stored identification data.

50. The system of claim 47, wherein the one or more implants are further configured to send back the initialization data within a predetermined time.

51. The system of claim 47, wherein the implant is configured to sense posture and/or movement data.

52. The system of claim 50, wherein the one or more implants are configured to be reinitialized when the reverse telemetry data has not been received by the external control unit within the predetermined time slot.

53. The system of claim 47, wherein the transmitted initialization data further comprising predetermined time slots for the one or more implants' forward and reverse transmission so that collisions between the transmissions are avoided.

54. The system of claim 47, wherein the control unit is further configured to initialize up to 20 implants.

55. The system of claim 47, wherein the one or more implant are configured to transmit the received initialization data back to the external control unit when the unique identification data transmitted by the control unit has been matched to the stored unique identification data of the one or more implants.

56. The system of claim 47, wherein the control unit is further configured to reinitialize the one or more implants in the event of implants power dropping below a predetermined level.

57. The system of claim 47, wherein the control unit reinitializes the one or more implants when the reverse telemetry data from the one or more implants has not been received within the predetermined time slot.

58. The system of claim 47, wherein the forward telemetry is via a frequency-shift keyed (FSK) signal and wherein the data is Manchester-encoded.

59. The system of claim 47, wherein the reverse telemetry received from the implant via an on-off keyed (OOK) bursts in the implant.

60. The system of claim 47, wherein the initialization data further include data defining a sequence of actions to be performed by the one or more implants in a frame.

61. The system of claim 60, wherein the control unit is further configured to transmit a frame sync signal to the one or more implants in order to trigger a start of a new frame.

62. The system of claim 60, wherein the control unit further configured to transmit one or more internal sync signals to the one or more implants in order to trigger one or more actions to be performed by the one or more implants according in each frame.

63. The system of claim 62, wherein the control unit is further configured to control frame duration and the timing for the one or more internal Sync signals transmitted in each frame.

64. The system of claim 63, wherein the control unit is further configured to encode by Manchester violation the frame onset and the timing of the one or more internal Sync signals.

65. The system of claim 47, wherein the one or more implants are configured to detect the electrical fields generated by different one or more implants, wherein the generated electrical fields are the product of the other implants delivering electrical current pulses.

66. The system of claim 47, wherein the control unit is further configured to dynamically adjust the stimulation data of the one or more implants based on the received data from the one or more implants.

67. The system of claim 47, wherein the received EMG data corresponds to the patient's residual voluntary movement of a muscle.

68. The system of claim 47, wherein the transmitted initialization data by the control unit further include mask data in order to prevent changing of certain values in the one or more implants according to dynamic data received subsequently.

69. The system of claim 68, wherein the mask data delimit the range of stimulation values by setting a bit in register of the one or more implants to remain unchanged.

70. The system of claim 47, wherein the control unit is further configured to receive positional data from the one or more of the implants.

71. The system of claim 70, wherein the control unit based on the received positional data is further configured to derive the coordinates of the one or more implants relative to positions of a plurality of coils installed external to patient's body.

72. The system of claim 70, wherein the positional data is gravitational data.

73. The implant of claim 47, wherein the one or more implants are further comprising a sensor that is configured to detect acceleration.

74. The system of claim 47, wherein the control unit is further configured to receive the M-waves measured by the one or more implants in response to the muscle stimulation.

75. The system of claim 47, wherein the control unit is further configured to trigger a spindle window after detection of the M-waves stops.

76. The system of claim 75, wherein the control unit is further configured to receive the electromyogram (EMG) data measured and integrated by the one or more implants after the spindle window is triggered.

77. The system of claim 47, wherein the implant is further configured to stimulate the muscle twice.

78. The system of claim 47, wherein the implant is further configured to collocate stimulation and sensing functions in the same implant.

* * * * *